United States Patent [19]

Iwasaki et al.

[11] Patent Number: 5,176,880
[45] Date of Patent: Jan. 5, 1993

[54] AUTOMATED BIOCHEMICAL ANALYZER

[75] Inventors: Shuji Iwasaki, Fujisawa; Toshi Kagayama, Yokohama; Kazuya Kamata, Ebina; Hidechika Hayashi, Yokohama, all of Japan

[73] Assignee: Tosoh Corporation, Yamaguchi, Japan

[21] Appl. No.: 555,728

[22] Filed: Jul. 23, 1990

[30] Foreign Application Priority Data

Jul. 24, 1989 [JP] Japan .................. 1-188738

[51] Int. Cl.⁵ ............... G01N 21/01; G01N 35/02
[52] U.S. Cl. .................... 422/63; 422/65; 422/67; 422/68.1; 436/47; 436/48; 436/49
[58] Field of Search ............... 422/63, 64, 65, 66, 422/67, 68.1; 436/47–49

[56] References Cited

U.S. PATENT DOCUMENTS

| 4,133,642 | 1/1979 | Nosaka et al. | 422/66 X |
| 4,263,001 | 4/1981 | Deutsch | 355/80 X |
| 4,428,673 | 1/1984 | Yoshida | 362/355 X |
| 4,680,457 | 7/1987 | Robertson | 235/470 |
| 4,751,184 | 6/1988 | Higo et al. | 422/65 X |
| 4,751,186 | 6/1988 | Baisch et al. | 422/67 X |
| 4,798,095 | 1/1989 | Itoh | 422/63 X |
| 4,889,982 | 12/1989 | Young et al. | 235/494 |
| 4,958,064 | 9/1990 | Kirkpatrick | 235/470 |
| 5,055,408 | 10/1991 | Higo et al. | 422/65 X |

FOREIGN PATENT DOCUMENTS

2148858  7/1987  Japan .

Primary Examiner—James C. Housel
Assistant Examiner—Arlen Soderquist
Attorney, Agent, or Firm—Nixon & Vanderhye

[57] ABSTRACT

An automated analyzer for automatically assaying a specific component in a sample by utilizing a top-opened reaction vessel containing a reagent capable of reacting with the specific component, and which is sealed with a seal foil on which a symbol for the reagent is shown; said analyzer comprising a seal foil breaker for breaking the seal foil, a sample dispenser for dispensing the sample to the vessel, and a detector for detecting a reaction signal caused by a reaction with the specific component and the reagent; a transfer device for transferring the reaction vessel and a symbol discriminator for discriminating the symbol shown on the seal foil, which is placed at a position on a transfer route of the reaction vessels transferred by the transfer device and at a position before the seal-foil breaker.

6 Claims, 5 Drawing Sheets

AUTOMATED BIOCHEMICAL ANALYZER

BACKGROUND OF THE INVENTION

1. Field of the Invention

The present invention relates to an automated analyzer for assaying a specific component in a sample. More particularly, the present invention relates to an automated analyzer for assaying a specific component in a sample by using a vessel which contains reagents therein.

2. Description of the Related Art

In recent years, automated analyzers are utilized in a variety of application fields. For example, an immunoassay apparatus for assaying an antigen or an antibody in a sample such as blood, plasma, and the like by utilizing an antigen or an antibody is utilized in a clinical diagnostic field.

In this specification, the present invention is described, as an example, regarding an immunoassay apparatus, particularly an automatic analyzer for conducting enzyme immunoassay by use of an enzyme-labelled antibody (or antigen). (Hereinafter the term "enzyme immunoassay" is referred to as "EIA".)

The EIA is a method for assaying a small amount of a component in a sample (Clinical Chemistry, Vol. 22, No. 8, 1243-1255, 1976). In a sandwich method therefor, the specific component to be assayed is captured by an appropriate antibody (or antigen) immobilized on a suitable solid phase material; then an enzyme-linked antibody or antigen (a conjugate) capable of reacting with the component to be assayed is brought into contact therewith to form an immune complex; the excess of the conjugate is removed; a substrate is added thereto which will output a detectable signal (such as change of absorbance, change of fluorescence intensity, etc.) by an activity of the enzyme; the signal is measured to determine quantitatively the amount of the enzyme according to a preliminarily prepared calibration curve; and from this the quantity of the specified component is estimated.

In this method, since different reagents, namely antibodies or antigens, are required corresponding to specific components to be assayed, the reaction vessels are provided in which different reagents are sealed up respectively corresponding to the specific components to be assayed, and are appropriately selected and used.

One of the example of automated analyzers for EIA is described in JP-A-62-148858 (The term "JP-A" as used herein means an "unexamined laid-open Japanese patent publication"), which comprises; means for dispensing a sample, means for breaking the top seal of a reaction vessel, means for dispensing a substrate, means for measuring, means for transferring reaction vessels.

In case where the concentration of the specific component is extremely high or extremely low, the detection ability of the reagent sealed in a reaction vessel is, usually, preliminarily adjusted to cover a wide range concentration of the specific component, or otherwise sample volume is adjusted according to the analyte.

In other words, conventionally, the assay is performed at a fixed sample volume for analytes which can be assayed at the sample volume, and thereafter the assay is performed for other analytes regarding the same or different samples at different sample volume.

In another practice, for the purpose of avoiding a repetition of the assay regarding the same sample, the sample volume is changed for every analyte by using an external input device such as a keyboard.

However, it is not desirable to perform the assay firstly for selected analytes for which the same sample volume is acceptable and then to perform the assay for other analytes for which a different sample volume is acceptable, because such operation takes much time and at least one operator have to be engaged therein. Further, the input operation of sample volumes by an external device for respective analytes requires at least one operator and artificial input errors may cause serious mistakes to assay results. These are the disadvantages which are to be solved by the present invention.

SUMMARY OF THE INVENTION

The present invention intends to provide an automated analyzer which utilizes reaction vessels containing respectively different reagents according to analytes, or specific components to be assayed.

The present invention provides an automated analyzer for automatically assaying a specific component in a sample by utilizing a top-opened reaction vessel; which contains a reagent capable of reacting with the specific component, and which is sealed with a seal foil on which a symbol for the reagent is shown: the analyzer comprises means for breaking the seal foil, means for dispensing a sample to the reaction vessel, means for measuring a reaction signal caused by a reaction with the specific component and the reagent, means for transferring the reaction vessel and means for discriminating the symbol shown on the seal foil, which is placed at a position on a transfer route of the reaction vessels transferred by the transferring means and at a position before the seal-foil breaking means.

The present invention further provides an automated analyzer, suitable for performing a sandwich EIA method, for automatically assaying a specific component in a sample by utilizing a top-opened reaction vessel containing a reagent capable of reacting with the specific component, which is sealed with a seal foil on which a symbol for the reagent is shown: the analyzer comprises means for breaking the seal foil, means for dispensing the sample to the vessel, means for separating a liquid component keeping a solid component in the reaction vessel, means for dispensing a second reagent other than the reagent sealed in the reaction vessel, means for detecting a reaction signal caused by a reaction with the specific component and the reagent, means for transferring the reaction vessel to the measuring system, and means for discriminating the symbol shown on the seal foil, which is placed at a position on a transfer route of the reaction vessels transferred by the transferring means and at a position before the seal foil breaking means.

DETAILED DESCRIPTION OF THE INVENTION

The present invention provides an automated analyzer for automatically assaying a specific component in a sample by utilizing a top-opened reaction vessel which contains a reagent capable of reacting with the specific component and which is sealed with a seal foil showing a symbol for the reagent. The analyzer of the present invention is useful, for example, as an automated analyzer for assaying a toxic substance in water, and as an automated analyzer for the above-mentioned immunoassay.

The symbols for denoting the reagents shown on the seal foil are not limited to technical terms of compounds or the like contained in the reagents. For example, alphabets like X and Y may be used. Any symbols are useful which enable discrimination of a reaction vessel for a specific component to be assayed from other reaction vessels. In the case of EIA, for example, the signals generated by the reaction may vary depending on the production lots even though a same quantity of a specific component is subjected to the assay. In such a case where each calibration curve suitable for the respective lot has to be selected, symbols for the production lot may be denoted to select the calibration curve for calculating assay results according to the production lot, and the analyzer may be controlled by use of the symbols.

In case of utilizing a cylindrical reaction vessel, it may be difficult to discriminate the symbol because the symbol would be upside-down as the result of rotation of the vessel. To meet the difficulty, it is preferred to show an additional symbol for indicating the direction of the symbol: for example, a lateral bar is shown under the symbol of a reagent.

A reagent sealed up in the reaction vessel is to be capable of reacting with a component to be assayed. A reagent to be used in EIA, for example, is an antibody if the component to be assayed is an antigen, or is an antigen if the component to be assayed is an antibody. In a "one-step sandwich method" and the like, there may be enclosed in the reaction vessel, as the reagent, an antibody or antigen acting on the component to be assayed and additionally an enzyme-labelled antibody or antigen. The reagent need not be limited to one compound but may be a mixture of compounds for assay of the specific component. In particular, in EIA, an antigen or antibody capable of acting on a specific component may be combined to a suitable solid-phase in order to separate excess of the conjugate. The solid-phase may be an inner wall of the reaction vessel, or may be a bead-like article. The reagent in this invention include such solid-phase.

The seal foil has desirably a superior sealing property and is made of a material which is breakable readily by means for breaking. The examples are metal foils such as of aluminum and the like, and laminated foils of aluminum with a plastic. Such a seal foil is heat-sealed or bonded on the external rim of the reaction vessel to close it tightly.

The means for breaking the seal foil to open the reaction vessel for the subsequent sample dispensing. For example, some means are disclosed in JP-A-62-273456, but the means for breaking is not limited thereto. Any means is useful therefor which is capable of removing the whole or a part of the seal-foil closing the reaction vessel to allow the subsequent operation to the reaction vessel.

The means for dispensing sample dispenses the sample to be assayed into the reaction vessel. The examples thereof are disclosed in JP-A-61-254833, JP-A-63-106567, etc. Methods or apparatuses for dispensing a sample with high accuracy are disclosed in JP-A-62-182665, etc.

The means for measuring detects a measurable signal generated in relation to the specific component in the sample to be assayed with reagents sealed in the reaction vessel. For example, in EIA, the antibody and the enzyme-labelled antibody as reagents react with an antigen to be assayed to form a complex, which will generate a signal in relation to the specific component when a substrate which causes a detectable change by an enzyme activity is added thereto. An example of such a device is disclosed in JP-A-62-034039. Color, absorbance, fluorescence, luminescence and the like are utilized as the signal. The measuring device is suitably constituted in accordance with the signal.

The means for transferring a reaction vessel transfers the reaction vessel to the positions for assaying the specific component in the sample as mentioned above. The means is exemplified by a transferring device having a constitution such as those disclosed by JP-A-62-148858. Such a transferring device is constituted of a plate for holding the reaction vessel and a means for transferring the plate. The transferring means of the present invention may be equipped with a temperature controlling means for maintaining the reaction vessel at a constant temperature, if necessary. To perform the EIA, for example, if the solid-phase contains a magnetic material as disclosed in JP-A-62-197425, a stirring means for stirring the solid-phase may be provided. Such a transferring means equipped with a temperature-controlling means and a stirring means is also disclosed in the aforementioned JP-A-62-148858, and a stirring means is disclosed, for example, in JP-A-62-036182.

The means for discriminating symbol is not specially limited if it is capable of recognizing the symbol shown on the seal foil. The means may be constituted of a light source, a lens for receiving the light of the light source reflected on the foil surface, and a means for discriminating the symbol from the intensity or the like of the reflected light, or otherwise the means may be a conventional bar-code reading device if conventional bar-code is used as the symbol. Specifically, a video camera may be utilized as the symbol discriminating means. The video camera may be of a black-and-white type or of a color type, and in particular, the number of picture elements is not limited. The camera may comprise a CCD (charge coupled device), or a vidicon tube. The one utilizing the CCD is preferable because of its relatively small size.

The discriminating means is placed at a position on a transfer route of the reaction vessel, and preceding the position where the seal is partly or wholly broken by the seal-foil breaking means.

If a video camera is used, a seal-foil illuminating means is preferably equipped in combination so that the video camera may discriminate the symbol satisfactorily. The seal-foil illuminating means is constituted, for example, of a light diffuser, a light source provided outside the light diffuser, and an opening. Such a seal-foil illuminating means is placed at a position between the video camera and the seal foil. Accordingly, the opening of the device comes to be located between the lens of the video camera and the seal foil. Since the output from the video camera is a picture image output, a video signal treating device, which is constituted of a memory and a computor, may be equipped for treating the output.

The light diffuser is in such a shape that it covers the nearly the whole of the seal foil (nearly $2\pi$ radian as the solid angle). The shape, for example, may be of a semisphere, a cylinder, a polygon, a polyhedron, or the like. The diffuser is made of a transparent material or a translucent material so that the seal foil may be illuminated by an external light source. Accordingly, the light projected by the external light source is diffused by the diffuser to illuminate the seal foil on the reaction vessel as well as the other parts of the interior of the diffuser. A portion of the light which is projected to the inside of the light diffuser is irregularly reflected further to illuminate the seal foil of the reaction vessel and other parts of the light diffuser, while another portion of the light transmits the light diffuser to illuminate the outside of the diffuser. The light diffuser is preferably roughened at the internal surface and/or the external surface, or made of a material which absorbs light less and is superior in light diffusion properties so that the transmitted light and reflected light can diffuse and illuminate uniformly the seal foil of the reaction vessel. The examples of the material include milky white glass (opal glass), milky white plastics, and the like. The light source may be a light emitting diode, an incandescent lamp, or the like.

The symbol-discriminating means described above enables the recognition of the reagent which is sealed up in the reaction vessel. According to the recognition of the reagent, the reaction vessel can be recognized as to which of the specific components the reagent is directed to. Therefore, the sample volume can be changed automatically to an optimum level by providing a controlling device to control the aforementioned sample dispensing means so that an optimum amount of the sample may be dispensed for assay of the specific component. In the present invention, not only to control the sample volume according to the symbol discriminated by the symbol-discriminating means, but an apparatus may also be constituted, for example, in such a manner that an additional reagent-injection means, which dispenses another reagent at an appropriate time during the assay, is controlled to be operated only when the reagent is needed. It is also possible to control a diluent-dispensing means to dilute the sample, and further control the diluent volume in the case where the content of the specific sample is presumed to be high and dilution of the sample is needed. Moreover, in EIA for example, when the signal generation by an enzyme in a conjugate is presumed to be low, it is also possible to control the analyzer to lengthen the reaction time of the enzyme with a substrate (the time from addition of the substrate into the reaction mixture to measurement of the signal), or lengthen the time of measurement in order to increase the enzyme reaction product.

Additionally to the automated analyzer described above, there may be provided a means for separating a liquid component with the solid-phase component being kept in the reaction vessel, or a means for dispensing a reagent other than the reagent sealed in the reaction vessel, thereby constituting a suitable automated analyzer for immunoassay, particularly for EIA. In the EIA, where a conjugate is used, the excess of the conjugate which has not combined to the specific component to be assayed has to be removed, because the reagent sealed in the reaction vessel comprises an antigen or an antibody capable of reacting with the specific component immobilized on an appropriate solid-phase and an enzyme labelled antigen or antibody (conjugate), and the specific component to be assayed comes to combine indirectly with the solid-phase according to an antigen-antibody reaction. For this reason, the aforementioned separating means is necessary.

The separating means is of any type which is capable of separating the component other than the solid-phase, namely a liquid component, in the reaction vessel. Such means are disclosed, for example, in JP-A-62-273453, JP-A-63-012959, etc.

In the EIA, the reagent other than the reagent sealed in the reaction vessel includes a substrate for the enzyme in the conjugate. A dispensing device for dispensing such a substrate is exemplified by the one disclosed, for example, in JP-A-62-148858.

The automated analyzer of the present invention may be equipped, if necessary, with a means for feeding the reaction vessel to the transferring apparatus as shown, for example, in JP-A-62-289763, and JP-A-63-015164, and a device for discharging the used reaction vessel as shown in JP-A-62-289762.

The present invention can perform the assay automatically without troublesome preliminary operations which are conventionally necessary before performing the assay.

By use of the analyzer of the present invention, only by setting a reaction vessel into the apparatus, the symbol shown on the seal foil of the reaction vessel is read out, the analyte is discriminated, and the subsequent operation may be performed such as the aforementioned change of the sample volume, and additional dispensation of a special reagent. Hence, the present invention can solve problems which impede automation of assay in conventional analyzers.

In particular, the assay time is shortened owing to needlessness of preliminary operation before the assay even when the analytes are to be selected for every sample independently.

Moreover, no artificial mistake occurs since there is no need for inputting any information about the analytes with a keyboard or the like.

DETAILED DESCRIPTION OF THE PREFERRED EMBODIMENT

The present invention is described in more detail referring to the figures.

Figure 1:
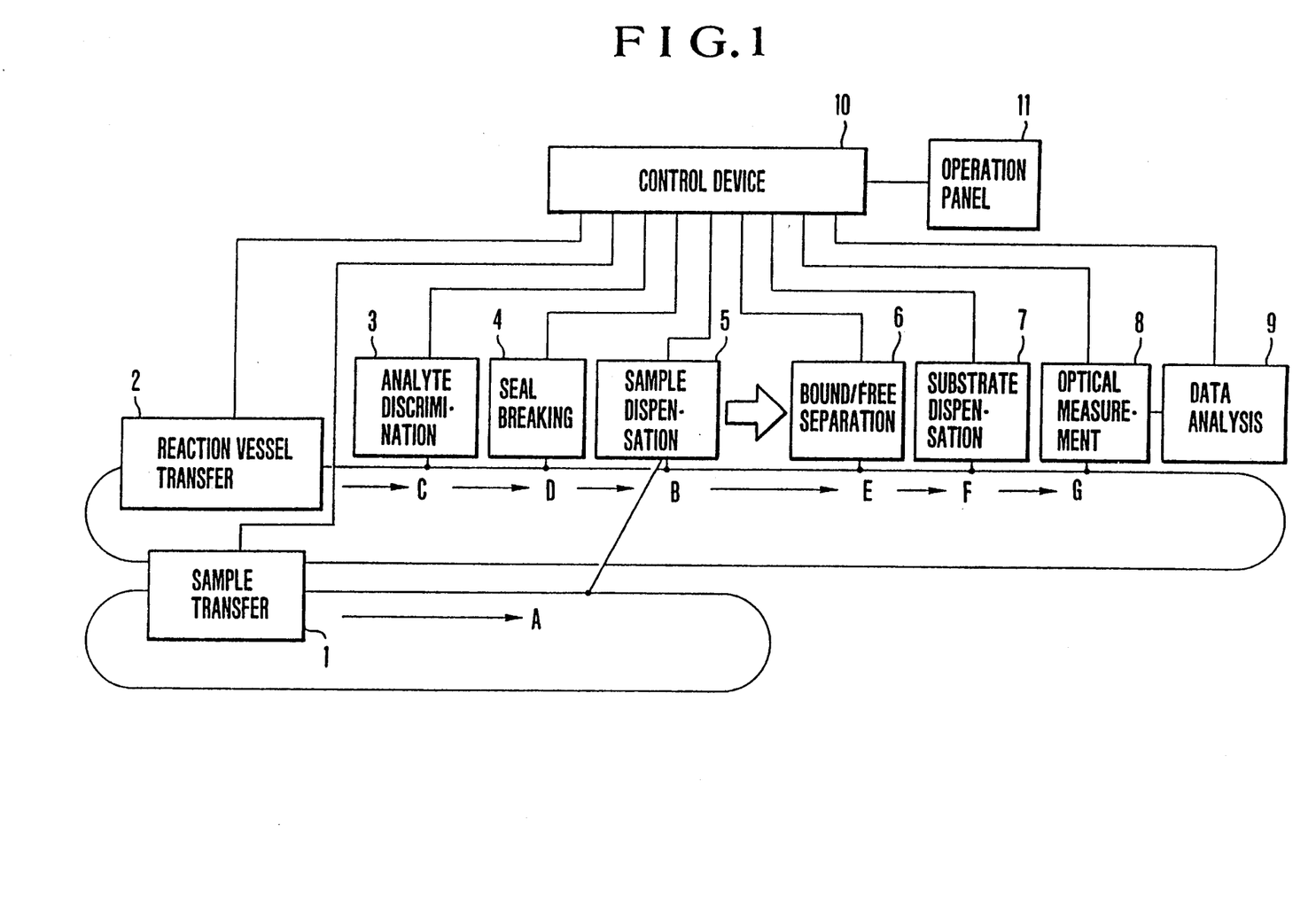
FIG. 1 shows a constitution of the automated analyzer of the present invention.

The automated analyzer of the present invention is applicable to various conventional analysis. As an example, FIG. 1 illustrates a constitution of an immunoassay analyzer for assaying an antigen or an antibody in the sample by an EIA method according to the present invention.

A sample such as blood, and plasma, is put into an appropriate container, and the container held by a holder or the container itself is transferred by a transferring device 1. The sample transferred to a sample dispensation position A on a sample transfer route is dispensed into a reaction vessel having reached the dispensation position B by means of a sample-dispensing means 5. The reaction vessel held by a suitable holder, or the reaction vessel itself, is transferred by reaction vessel transferring device 2 in the direction denoted by the arrow mark. On the transfer route, the following means are arranged: a symbol-discriminating device 3 at an analyte-discrimination position C, a seal-foil-breaking device 4 at a seal-breaking position D, a sample-dispensing device 5 at a dispensation position B, a separating device 6 at a Bound/Free (B/F) separation position E, a dispensing device 7 at a substrate-dispensation position F, and analyzing device 8 at a optical measurement position G. The measuring system and the transfer device are controlled by a control device 10.

Firstly, the symbol shown on the seal foil of the reaction vessel is discriminated at the position C. The information from the discrimination device is transmitted to a separate control device 10. Subsequently, the seal foil is broken, and the sample is dispensed. The sample volume to be dispensed is controlled by the control device in response to the information from the discriminating device so as to feed a suitable quantity of the specific component (or the analyte) to be assayed. After the dispensation of the sample, the reaction vessel is transferred to the Bound/Free (B/F) separation position E where the excess of the conjugate in the reaction vessel is separated. Then the substrate for the enzyme is dispensed, and the signal generated in relation to the specific component is measured by the measuring device 8 at the optical measurement position C.

This apparatus is equipped with a data-analyzing device 9 for calculation regarding the measurement signal on the basis of a preliminarily inputted form, and an inputting device (an operating panel 11) for accessing the data-analysis result or directing start or stop of the apparatus.

Figure 2:
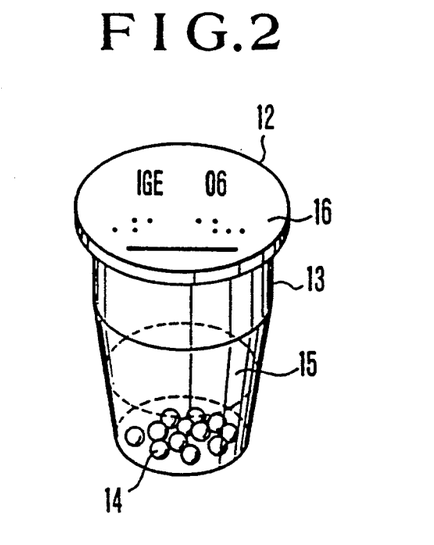
FIG. 2 shows an external shape of the reaction vessel and a reagent sealed in the vessel.

FIG. 2 illustrates a reaction vessel applicable to the analyzer of the present invention. The reaction vessel 12 contains a solid phase 14 for B/F separation performed in EIA, an antibody (or an antigen; not shown in the figure) immobilized on the solid phase, and a conjugate (not shown in the figure). Usually, such reagents for EIA are lyophilized with optional stabilizing agent into a form of a bulk 15 as a whole, and is enclosed in the vessel. The side face 13 of the reaction vessel is not specially limited in its shape, etc., but is preferably in a shape suitable for being held tightly by a holder if the vessel is transferred by means of a holder.

Figure 6:
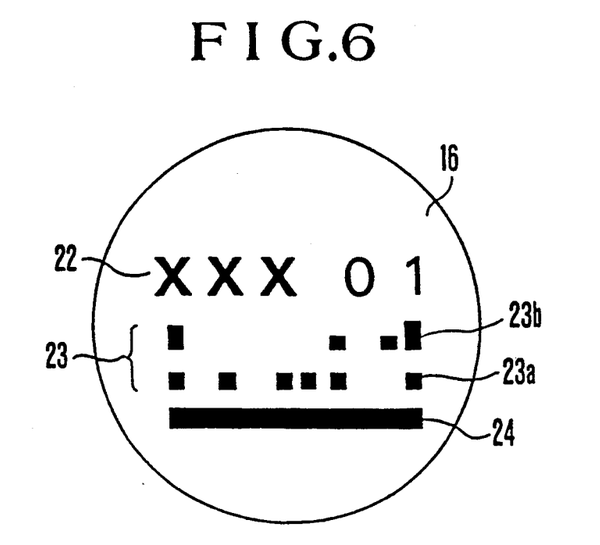
FIG. 6 and FIG. 7 show examples of discrimination symbols printed on the seal foil.
Figure 7:
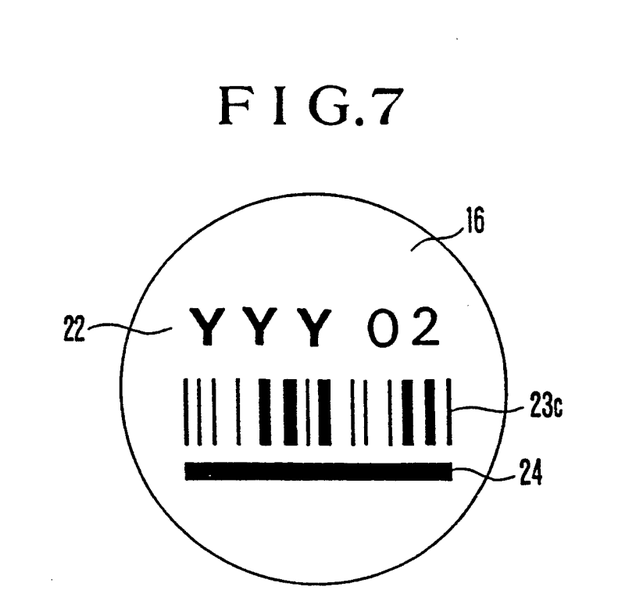

On the seal foil 16 sealing the reaction vessel, a symbol is shown which denotes the reagent sealed up in the reaction vessel. In this example, the symbol "IGE" denoting immunoglobulin E together with the symbol "06" denoting a lot number of the reagent shows the reagent sealed up in the reaction vessel. While such symbols may be used which can be discriminated visually by an operator, a symbol like X, or Y which does not have meaning by itself may be used as shown in FIG. 6 and FIG. 7.

Figure 3:
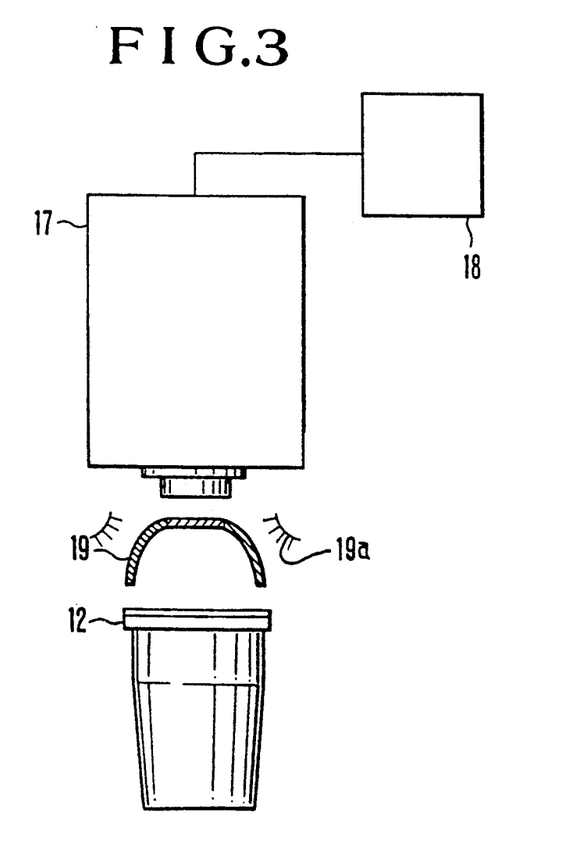
FIG. 3 illustrates an outline of means for discriminating the symbol.
Figure 4A:
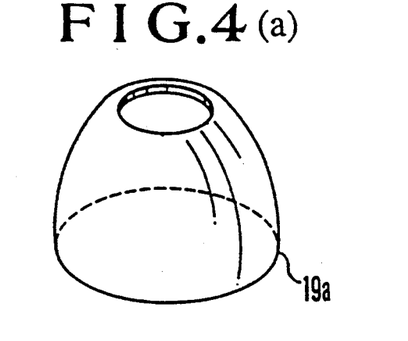
FIGS. 4(a)-4(d) show light diffusers.
Figure 4B:
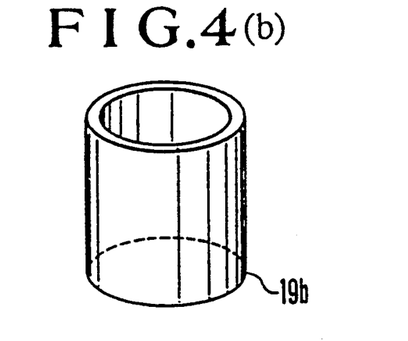
Figure 4C:
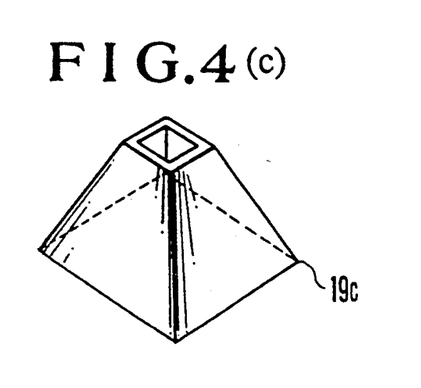
Figure 4D:
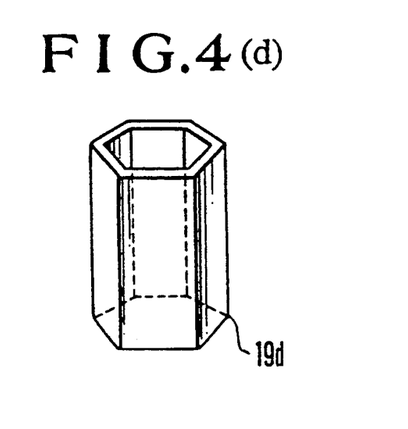

FIG. 3 illustrates an arrangement at the analyte discrimination position C in FIG. 1. A light diffuser 19 is placed above a reaction vessel 12 so as to cover the seal foil, and further above it, a video camera 17 is placed. An opening (not shown in the figure) is provided at a portion of the light diffuser on the line from the seal foil to the lens of the video camera. A light source 19a directs light onto the seal disc 16 for reflection into the video camera. The image output from the video camera is transmitted to a video signal processor 18, and further transmitted to the control device shown in FIG. 1. The video signal processor may be constituted of a memory and a computer.

FIG. 4 illustrates light diffusers for constituting a seal-foil-illuminating device which is preferably combinedly used with a symbol-discriminating device comprising a video camera in the present invention. The illustrated light diffusers are in shapes of a semisphere (a), a cylinder (b), a pyramid (c), and a polyhedron (d).

Figure 5:
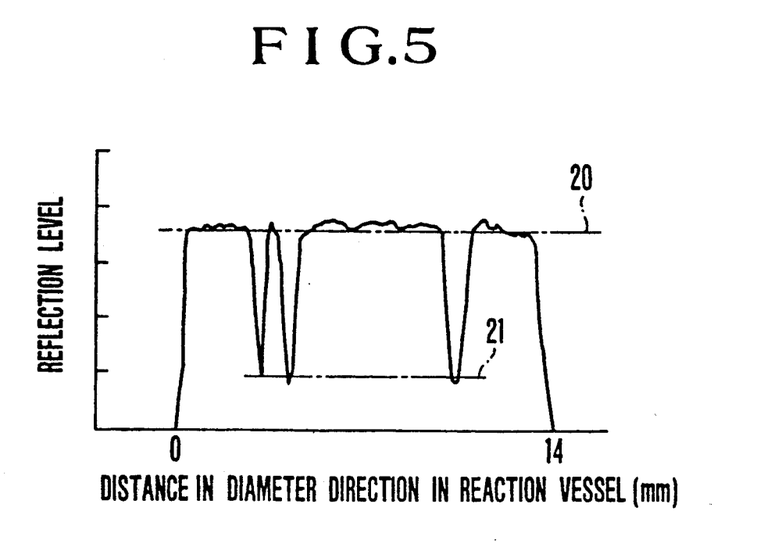
FIG. 5 shows an example of a video image, where the abscissa shows the distance in diameter direction in the reaction vessel, and the ordinate shows reflection level of reflected light.

FIG. 5 shows an example of video images in the case where, referring to FIG. 4, the reaction vessel is sealed with a circular seal foil of 7 mm in radius, a cylindrical light diffuser of 15 mm in diameter and 30 mm in height made of milky white plastic is placed above the reaction vessel, and the seal foil is illuminated by each five light-emitting-diodes as light sources placed outside the light diffuser at the two heights of 10 mm and 20 mm from the bottom face of the diffuser and at an equal spacing corresponding to a central angle of 72°. In this Example, the image is obtained by use of a black-and-white CCD camera. The background is illuminated uniformly. The reflection level 21 of the symbol is clearly distinguishable from the reflection level 20 of the background.

FIG. 6 and FIG. 7 show examples of symbols shown on the seal foils. On the seal foil 16, a symbol 22 denoting an analyte, and production lot of the reagent sealed up in the reaction vessel, a dots symbol 23a, 23b therefor, or a bar-code denotation 23c is shown. In both figures, the lateral lines 24 at the lower sides are symbols for detecting the direction of the symbols or of the reaction vessel.

Figure 8:
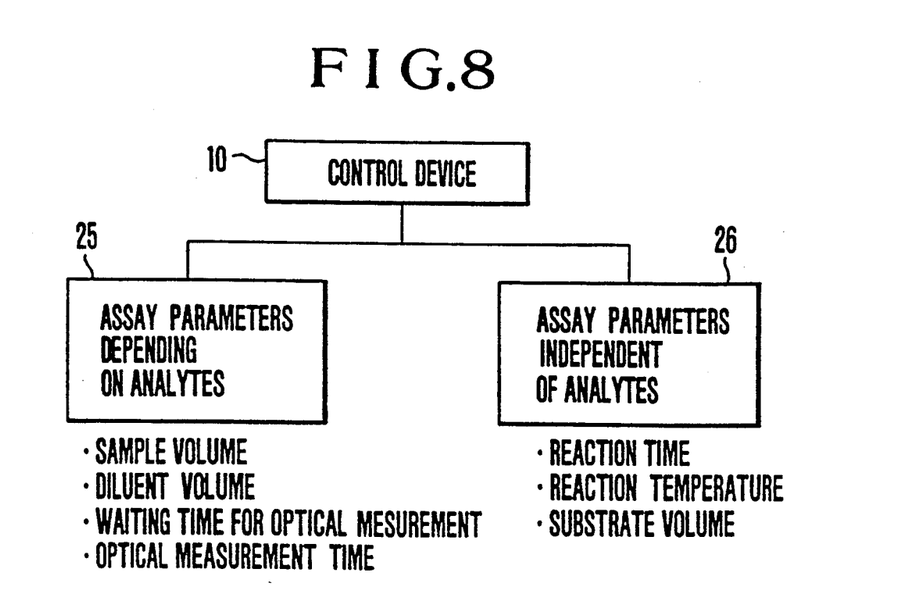
FIG. 8 shows assay parameters depending on or independent of analytes.

FIG. 8 shows the assay parameters 25 which depend on analytes and the assay parameters 26 which are independent of analytes. The controlling device 10, on receiving a signal from the symbol-discriminating device, decides the operations to be changed for the reaction vessel showing the symbol, and control the measurement apparatus to perform the assay.

Figure 9:
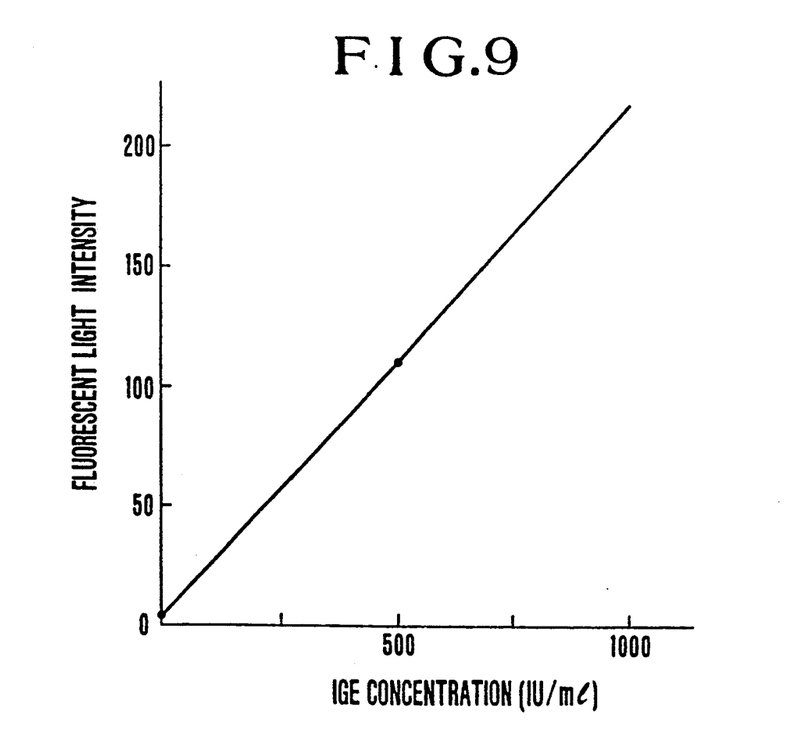
FIG. 9 shows an example of a calibration curve showing the relation of a detected signal with a concentration of a specific component to be assayed.

FIG. 9 shows an example of the preliminarily prepared calibration curves which gives a correlation between the signal and the concentration of the specific component (IGE) in EIA. Such data are stored in a data analyzer 9 in FIG. 1, for example.

Such a calibration curve may depend on the production lots provided for assaying the same analyte. Accordingly, the data processor may be constituted to store several calibration curves for one anaylte, and to select one of the calibration curves suitable for the lot in accordance with the symbols shown on the reaction vessel.

What is claimed is:

1. An automated analyzer for automatically assaying a specific component in a sample by utilizing a top-opened reaction vessel containing a reagent capable of reacting with the specific component, and which is sealed with a seal foil on which a symbol for the reagent is shown: said analyzer comprising means for breaking the seal foil, means for dispensing the sample to the vessel, and means for detecting a reaction signal caused by a reaction with the specific component and the reagent; means for transferring the reaction vessel along a predetermined transfer route for sequentially transferring said vessel through said seal breaking means and said dispensing means, and means for discriminating the symbol shown on the seal foil, along said transfer route before the seal-foil breaking means;

the symbol-discriminating device comprising a video camera placed in a direction substantially perpendicular to the seal foil closing tightly the opening of the reaction vessel on the transferring device for the reaction vessel, and a seal-foil-illuminating device placed between the seal foil and the video camera;

the seal-foil-illuminating device comprising a light source positioned such that light from the light source is reflected by the seal foil into the video camera and a light diffuser positioned between the light source and seal foil so as to cover the seal foil, said light diffuser having an opening in a portion thereof which is between the video camera and the seal foil.

2. The automated analyzer of claim 1, wherein a control device for controlling the sample-dispensing device is provided to control the sample dispensing volume into the reaction vessel performed by the sample-dispensing device in accordance with the symbol discriminated by the symbol-discriminating device.

3. The automated analyzer according to claim 2 wherein said reagent in said reaction vessel is for antigen-antibody reaction with a specific component of a sample to be assayed.

4. An automated analyzer for automatically assaying a specific component in a sample by utilizing a top-opened reaction vessel which contains a reagent capable of reacting with the specific component, and having a top-face opening which is sealed with a seal foil on which a symbol for the reagent is shown; said analyzer comprising means for breaking the seal foil, means for dispensing the sample to the vessel, means for separating a liquid component keeping a solid component in the reaction vessel, means for dispensing a second reagent other than the reagent sealed in the reaction vessel, and means for detecting a reaction signal caused by a reaction with the specific component and the reagent; means for transferring the reaction vessel to the measuring system; and means for discriminating the symbol shown on the seal foil, which is placed at a position on a transfer route of the reaction vessels transferred by the transferring means and at a position before the seal-foil breaking means, the symbol-discriminating device comprising a video camera placed in a direction substantially perpendicular to the seal foil closing tightly the opening of the reaction vessel on the transferring device for the reaction vessel, and a seal-foil-illuminating device placed between the seal foil and the video camera;

the seal-foil-illuminating device comprising a light source positioned such that light from the light source is reflected by the seal foil into the video camera and a light diffuser positioned between the light source and seal foil so as to cover the seal foil, said light diffuser having an opening in a portion thereof which is between the video camera and the seal foil.

5. The automated analyzer of claim 4 wherein a control device for controlling the sample-dispensing device is provided to control the sample dispensing volume into the reaction vessel performed by the sample-dispensing device in accordance with the symbol discriminated by the symbol-discriminating device.

6. The automated analyzer according to claim 5 wherein said reagent in said reaction vessel is for antigen-antibody reaction with a specific component of a sample to be assayed.

* * * * *